United States Patent
Rice et al.

(10) Patent No.: US 8,142,490 B2
(45) Date of Patent: Mar. 27, 2012

(54) STENT SEGMENTS AXIALLY CONNECTED BY THIN FILM

(75) Inventors: Carolyn Rice, Los Gatos, CA (US);
Craig Bonsignore, Pleasanton, CA (US)

(73) Assignees: Cordis Corporation, Bridgewater, NJ (US); Advanced Bio Prosthetic Surfaces, Ltd., Dallas, TX (US)

( * ) Notice: Subject to any disclaimer, the term of this patent is extended or adjusted under 35 U.S.C. 154(b) by 210 days.

(21) Appl. No.: 11/923,308

(22) Filed: Oct. 24, 2007

(65) Prior Publication Data

US 2009/0112306 A1    Apr. 30, 2009

(51) Int. Cl.
*A61F 2/06* (2006.01)
(52) U.S. Cl. ..................... 623/1.29; 623/1.13
(58) Field of Classification Search ............. 623/1.44, 623/1.1, 1.11, 1.13, 1.15, 1.27–1.35
See application file for complete search history.

(56) References Cited

U.S. PATENT DOCUMENTS

| 3,585,707 | A | | 6/1971 | Stevens | |
|---|---|---|---|---|---|
| 4,665,906 | A | | 5/1987 | Jervis | |
| 4,925,445 | A | | 5/1990 | Sakamoto et al. | |
| 5,045,072 | A | | 9/1991 | Castillo et al. | |
| 5,122,154 | A | | 6/1992 | Rhodes | |
| 5,254,107 | A | | 10/1993 | Soltesz | |
| 5,607,464 | A | * | 3/1997 | Trescony et al. | 623/1.29 |
| 5,609,629 | A | | 3/1997 | Fearnot et al. | |
| 5,634,941 | A | * | 6/1997 | Winston et al. | 623/1.11 |
| 5,653,745 | A | * | 8/1997 | Trescony et al. | 623/1.29 |
| 5,824,049 | A | | 10/1998 | Ragheb et al. | |
| 5,922,019 | A | * | 7/1999 | Hankh et al. | 623/1.13 |
| 6,071,307 | A | * | 6/2000 | Rhee et al. | 623/1.13 |
| 6,099,558 | A | * | 8/2000 | White et al. | 623/1.16 |
| 6,139,573 | A | * | 10/2000 | Sogard et al. | 623/1.13 |
| 6,174,329 | B1 | | 1/2001 | Callol et al. | |
| 6,197,013 | B1 | | 3/2001 | Reed et al. | |
| 6,261,320 | B1 | | 7/2001 | Tam et al. | |
| 6,287,335 | B1 | * | 9/2001 | Drasler et al. | 623/1.28 |
| 6,315,794 | B1 | | 11/2001 | Richter | |
| 6,371,982 | B2 | * | 4/2002 | Berg et al. | 623/1.4 |
| 6,475,234 | B1 | | 11/2002 | Richter et al. | |
| 6,533,810 | B2 | * | 3/2003 | Hankh et al. | 623/1.16 |
| 6,626,938 | B1 | * | 9/2003 | Butaric et al. | 623/1.28 |

(Continued)

FOREIGN PATENT DOCUMENTS

WO    WO 2006/034114 A2    3/2006

(Continued)

OTHER PUBLICATIONS

International Search Report dated Jul. 12, 2010 corresponding to PCT/US2008/081192.

(Continued)

*Primary Examiner* — Alvin J. Stewart

(57) ABSTRACT

In accordance with the present invention, there is provided a stent for insertion into a vessel of a patient. The stent has a front and back open ends and a longitudinal axis extending therebetween. The stent has a plurality of adjacent hoops that are held in alignment with the longitudinal axis between the front and back open ends by a thin film tube. The hoops are attached to either the inner or outer surface of the thin film tube. The stent is compressed into a first smaller diameter for insertion into the vessel with a delivery tube and a second larger diameter for deployment into the vessel. The inventive stent can be retracted into the delivery tube if it is improperly deployed.

16 Claims, 10 Drawing Sheets

U.S. PATENT DOCUMENTS

| | | | |
|---|---|---|---|
| 6,638,301 B1 | 10/2003 | Chandrasekaran et al. | |
| 6,699,277 B1 * | 3/2004 | Freidberg et al. | 623/1.13 |
| 6,770,086 B1 * | 8/2004 | Girton | 623/1.13 |
| 6,865,810 B2 | 3/2005 | Stinson | |
| 6,884,429 B2 | 4/2005 | Koziak et al. | |
| 6,887,265 B2 | 5/2005 | Richter et al. | |
| 6,911,040 B2 * | 6/2005 | Johnson et al. | 623/1.13 |
| 6,936,066 B2 * | 8/2005 | Palmaz et al. | 623/1.13 |
| 6,938,668 B2 | 9/2005 | Whicher et al. | |
| 6,939,376 B2 | 9/2005 | Shulze et al. | |
| 7,077,859 B2 | 7/2006 | Sirhan et al. | |
| 7,195,641 B2 * | 3/2007 | Palmaz et al. | 623/2.18 |
| 7,226,474 B2 * | 6/2007 | Iancea et al. | 623/1.13 |
| 7,261,735 B2 | 8/2007 | Llanos et al. | |
| 7,291,165 B2 | 11/2007 | Rosenthal et al. | |
| 7,294,147 B2 * | 11/2007 | Hartley | 623/1.13 |
| 7,309,349 B2 | 12/2007 | Jackson et al. | |
| 7,396,538 B2 | 7/2008 | Granada et al. | |
| 7,713,573 B2 | 5/2010 | Owens et al. | |
| 7,806,924 B2 | 10/2010 | Falotico et al. | |
| 7,807,211 B2 | 10/2010 | Hossainy et al. | |
| 7,811,300 B2 | 10/2010 | Feller, III et al. | |
| 7,837,726 B2 | 11/2010 | Von Oepen et al. | |
| 7,854,760 B2 | 12/2010 | Molaei et al. | |
| 2002/0051730 A1 | 5/2002 | Bodnar et al. | |
| 2002/0082676 A1 | 6/2002 | You | |
| 2002/0133183 A1 | 9/2002 | Lentz et al. | |
| 2003/0018381 A1 | 1/2003 | Whitcher et al. | |
| 2003/0104028 A1 | 6/2003 | Hossainy et al. | |
| 2003/0163017 A1 | 8/2003 | Tam et al. | |
| 2004/0098094 A1 * | 5/2004 | Boyle et al. | 623/1.13 |
| 2004/0249445 A1 | 12/2004 | Rosenthal et al. | |
| 2005/0106212 A1 | 5/2005 | Gertner et al. | |
| 2005/0113903 A1 | 5/2005 | Rosenthal et al. | |
| 2005/0137677 A1 | 6/2005 | Rush | |
| 2005/0233062 A1 | 10/2005 | Hossainy et al. | |
| 2005/0267566 A1 * | 12/2005 | Rioux et al. | 623/1.28 |
| 2006/0149365 A1 | 7/2006 | Fifer et al. | |
| 2006/0224234 A1 | 10/2006 | Jayaraman | |
| 2006/0229711 A1 | 10/2006 | Yan et al. | |
| 2006/0259126 A1 | 11/2006 | Lenz | |
| 2006/0259131 A1 | 11/2006 | Molaei et al. | |
| 2006/0265052 A1 | 11/2006 | You | |
| 2006/0276884 A1 | 12/2006 | Lye et al. | |
| 2006/0276885 A1 | 12/2006 | Lye et al. | |
| 2007/0077347 A1 | 4/2007 | Richter | |
| 2007/0123977 A1 | 5/2007 | Cottone et al. | |
| 2007/0207186 A1 | 9/2007 | Scanlon et al. | |
| 2007/0219642 A1 | 9/2007 | Richter | |
| 2007/0276470 A1 * | 11/2007 | Tenne | 623/1.38 |
| 2008/0071348 A1 | 3/2008 | Boismier et al. | |
| 2008/0294246 A1 | 11/2008 | Scheuermann et al. | |
| 2011/0001271 A1 | 1/2011 | Hossainy et al. | |
| 2011/0008529 A1 | 1/2011 | Hossainy et al. | |

FOREIGN PATENT DOCUMENTS

| | | |
|---|---|---|
| WO | WO 2006/034301 A1 | 3/2006 |
| WO | WO 2007/022495 A1 | 2/2007 |

OTHER PUBLICATIONS

Office Action mailed Mar. 8, 2011 in related U.S. Appl. No. 12/608,023.

* cited by examiner

STENT SEGMENTS AXIALLY CONNECTED BY THIN FILM

FIELD OF THE INVENTION

The present invention relates to an expandable intraluminal grafts ("stents") for use within a body passageway or duct which are particularly useful for repairing blood vessels that have been narrowed or occluded by disease. The present invention relates even further to such stents which are self-expanding and made from a super elastic material such as Nitinol.

BACKGROUND OF THE INVENTION
BACKGROUND

Percutaneous transluminal coronary angioplasty (PTCA) is a therapeutic medical procedure used to increase blood flow through the coronary artery and can often be used as an alternative to coronary by-pass surgery. In this procedure, the angioplasty balloon is inflated within the stenosed vessel in order to disrupt the wall components of the vessel to obtain an enlarged lumen. With respect to arterial stenosed lesions, the relatively incompressible plaque remains unaltered, while the more elastic medial and adventitial layers of the body passageway stretch around the plaque.

Self-expanding stents that are radially and axially flexible have been developed that are composed of a plurality of flexible elements that form a self-expanding helix. These stents are implanted to open or dilate tubular structures and have been used for damaged blood vessels, biliary ducts, and other similar organs. The stents are an improvement over PTCA procedures because the implanted stent holds the intimal flap and plaque against the inner wall of the vessel preventing it from blocking the vessel.

Prior art stents have some functional limitations due to their current design. For example, the prior art stent can collapse when it is bent around a sharp angle. What is needed is an improved stent that is more flexible and can be implanted in tightly bent vessels.

SUMMARY OF THE INVENTION

The present invention is an improved stent has good radial strength to hold the vessel open and greater flexibility that is suitable for implantation in more sharply bent vessels. The inventive stent includes a thin film tube that is attached to a plurality of hoops axially aligned between the front and back ends of the stent. Each of the hoops includes a plurality of longitudinal struts and a plurality of loops connecting adjacent struts. The struts and loops form a continuous serpentine pattern around the diameter of the hoop. The thin film tube holds the hoops together and also provide a space between the adjacent hoops. The stent has a compressed diameter for simplified implantation into the patient and an expanded diameter that is assumed after it is inserted into the patient. The inventive stent is a tubular member that has front and back open ends and a longitudinal axis extending therebetween.

The inventive stent has improved flexibility because the adjacent hoops are held together with a flexible thin film tube rather than bridges. The thin film tube is more flexible than the bridges because the thin film tube is much thinner. The thin film spans the area between the adjacent hoops and can easily fold when compressed. This improved flexibility allows the stent to be easily moved through blood vessels and deployed in a bent vessel within the patient. In contrast, the more rigid bridges that couple the adjacent hoops restrict the bending radius of the prior art stents.

The inventive stent has a first smaller diameter for insertion into the vessel and a second larger diameter for deployment into the vessel. The hoops of the stent include struts and loops that are bendable so that the hoops can be compressed to the smaller diameter. In the compressed state, the loops are bent so that the adjacent struts are substantially parallel to the longitudinal axis of the stent and placed in very close proximity with only a small gap between them. The thin film tube is attached to the hoops and portions of the thin film tube may be folded between the gaps between the struts and loops when the stent are compressed to the smaller diameter. In the expanded state, the hoops expand thereby forming larger gaps between the struts and loops. Likewise, the thin film tube expands with the hoops to cover the gaps formed between the struts and loops. The thin film tube also traps plaque and other deposits between the stent and the vessel wall. In contrast, prior art stents have gaps between the loops, struts and bridges that may not trap small pieces of plaque and debris.

In a preferred embodiment, the thin film tube and hoops are made of a super elastic metal alloy that can change from the martensitic molecular phase to the austenitic phase by changing the stent temperature. For implantation, the stent is compressed and loaded onto a delivery tube apparatus. The delivery device holds the stent in the compressed state and is used to transport the stent to a specific area within a patient. The stent is deployed at a damaged area of the blood vessel by releasing the stent from the delivery apparatus. In an embodiment, the delivery device pushes the stent out of the delivery tube while simultaneously pulling the delivery tube back to expose the stent. This allows the inventive stent to expand radially to the inner diameter of the blood vessel without any axial movement relative to the vessel. The expanded stent remains axially stationary relative to the blood vessel to avoid damage during the deployment process.

The stent may have radio opaque markers which allow the surgeons to monitor the location for the stent during the delivery procedure. By watching the position of the stent within the patient, the stent can be positioned within the vessel more accurately.

The radio opaque markers can be attached to the stent by welding the markers to the stent. Alternatively, the markers may be attached with adhesives, mechanical fasteners or other coupling systems.

Another capability is that the inventive stent can be partially deployed and then retracted if it is improperly positioned within a patient. The stent can then moved to the proper location and redeployed. The inventive stent is retracted by pulling the stent back into the delivery tube which causes the stent to be recompressed within the delivery tube so that it can be moved the proper position and redeployed.

The retraction capability may require longer stents so any positioning error can be detected before the stent is fully deployed and irretrievable. In this embodiment, the delivery device is able to cut the inventive stent around the thin film tube between any adjacent hoops. In this embodiment, the location of a partially deployed stent is monitored and if the position is correct, the portion of the stent in the delivery device is cut and the partially deployed section of the stent remains in the vessel. If the stent is improperly positioned, it can be retracted and repositioned as described above.

Although the inventive stent is described as being made from a super elastic alloy, in an embodiment, the stent can also be made from more traditional stent materials that are not self expanding, such as stainless steel, cobalt-chromium, etc.

In these embodiments an expansion mechanism is required to expand the stent after it is placed in the patient. The balloon is in the inner of the stent during the implantation process. Markers may be attached to the stent so the location can be determined before the stent is expanded. A tube extends from the balloon to a pump that inflates the balloon and expands the stent. The balloon and delivery apparatus are removed from the patient after the stent is implanted.

BRIEF DESCRIPTION OF DRAWINGS

The foregoing and other aspects of the present invention will best be appreciated with reference to the detailed description of the invention in conjunction with the accompanying drawings, wherein.

DETAILED DESCRIPTION

The inventive stent includes a plurality of hoops and a thin film tube which are made of a super elastic metal alloy or more traditional materials such as stainless steel, cobalt-chromium, etc. Although the super elastic alloy is described as Nitinol, any alloy with similar super elastic properties may be used. In the preferred embodiment, the hoops of the inventive stent are made from Nitinol tube stock which is commercially available from a number of suppliers including Nitinol Devices and Components, Fremont Calif. Alternatively, the Nitinol tube used to form the hoops may be fabricated through a vapor deposition process. The thin film tube is preferably made through a deposition process, but may also be made from very thin tube stock.

Vapor deposition, as used herein, refers to any process of depositing metals and metal compounds from a source to a substrate or target by dissipating metal ions from the source in a vaporous medium. The vapor deposition process builds a layer of Nitinol by depositing molecules of the alloy onto a cylindrical mandrel in a vacuum chamber. Examples of vapor deposition processes that may be used to make the present invention include evaporation vapor deposition, sputtering deposition, chemical vapor deposition, etc.

In the evaporation vapor deposition process, vapor is generated by heating a source material to a temperature to cause the vaporization thereof. The evaporating metal atom leaves the surface of the Nitinol source material in a straight line. Therefore, the highest quality deposition layers are deposited when the source-to-substrate distance is less than the mean path distance between collisions of the vaporized metal and the surrounding vacuum chamber. The substrate may be rotated or translated during the evaporation process so that a uniform Nitinol layer is deposited on the substrate.

In the sputtering process, a source material is placed in a vacuum chamber with a substrate material. A radio-frequency power source gives the substrate has a positive charge relative to the Nitinol source material. The source material is bombarded with inert gas ions from an ion beam or a plasma discharge to cause the source material to dislodge. These dislodged atoms are then deposited onto the substrate to form the thin film layer.

In the chemical vapor deposition process, reactant gases that may be diluted in a carrier gas are injected into a reaction chamber. The gas mixture is heated and the atoms are deposited on a mandrel. The thickness of the hoops may range from about 0.005 to about 0.1 inch. The thickness of the thin film tube is less than the thickness of the hoops and may range from about 0.0001 to about 0.05 inch. Although the hoops and thin film tube may vary in thickness, the hoops are generally much thicker than the thin film tube. The deposition continues until the desired thickness is formed. The Nitinol tube is removed from the mandrel before being machined.

Figure 1:
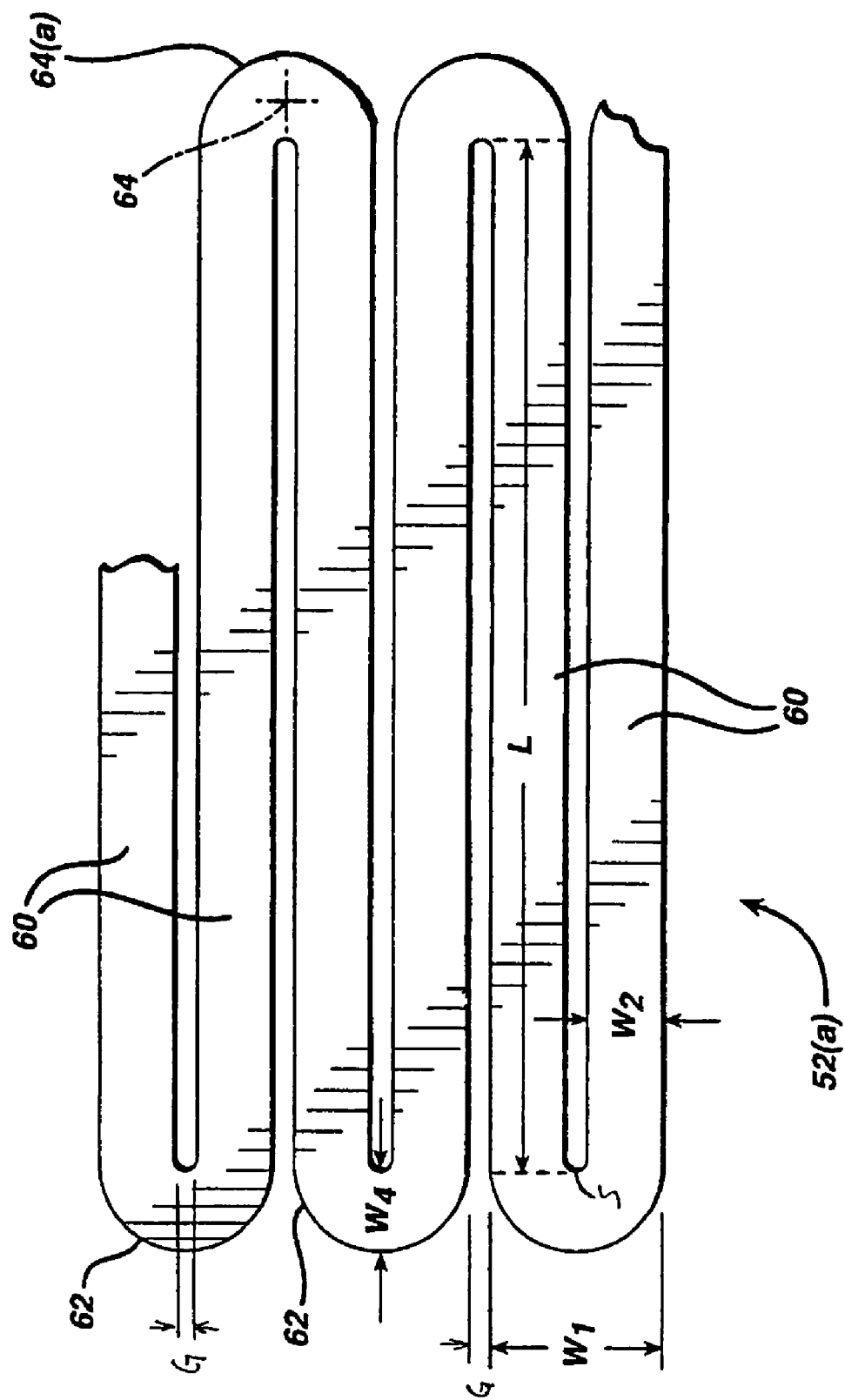
FIG. 1 is a flat view of a portion of a hoop in the compressed state.

As discussed above, the hoops have a first small diameter for insertion into a vessel and a second larger diameter for deployment into the vessel. In all figures, like numerals indicate the same element throughout the views. With reference to FIG. 1, a sectional view of a hoop 52 in the compressed state is illustrated. The hoops 52 each include a plurality of longitudinal struts 60 and a plurality of loops 62 that connect the adjacent struts 60. The adjacent struts 60 are connected with loops 62 in an alternating pattern at opposite ends of the struts 62, forming a serpentine or "S" shaped pattern. In the compressed state, the loops 62 are substantially semi-circular and creates very sharp bend. The angle between the struts 60 may only be about 0° to 5°. Thus, the space between the struts 60 is small because the 180° bends of the loops 62 cause the struts 60 to be compressed close to each other.

Figure 2:
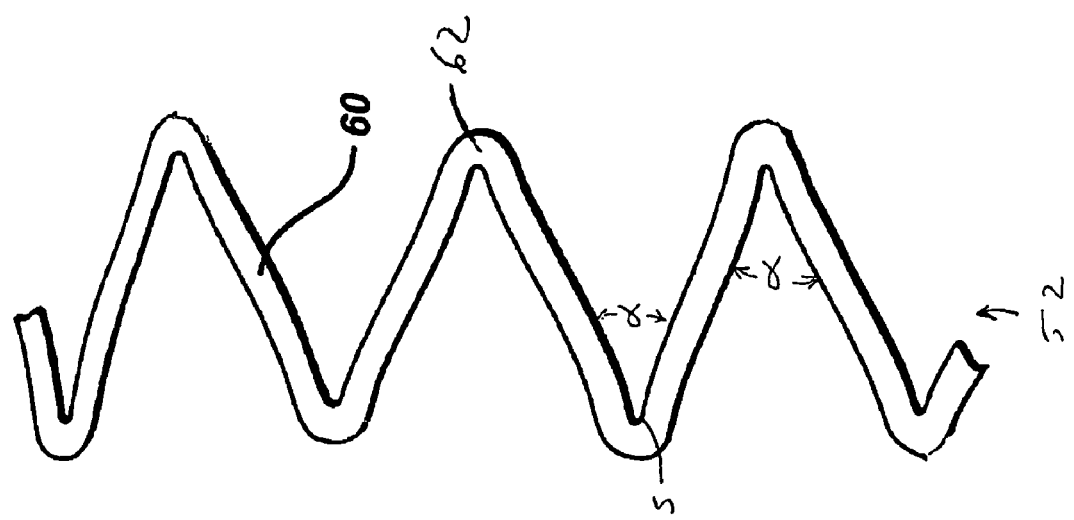
FIG. 2 is a flat view of a portion of a hoop in the expanded state.

With reference to FIG. 2, a sectional view of a hoop 52 in the expanded state is illustrated. The expansion of the hoop 52 may only be in the circumference and not the width. In the expanded state, the angle $\alpha$ between adjacent struts 60 connected by the loops 62 increases from a compressed angle of about 0° to 5° to an expanded angle of about 30° to 70°. The expanded angle $\alpha$ of the loops 62 causes the struts 60 to separate and causes the hoop 52 to expand in circumference and diameter. As the circumference of the hoop 52 expands, the width of the hoop 52 get narrower because the struts 60 are angled across the width rather than running perpendicular across the widths.

The geometry of the struts improves the distribution of strain throughout the hoops. The number of struts and loops as well as the design of these components are important factors when determining the working properties and fatigue life of the stent. Hoops that have a large quantity of smaller sized struts have greater radial rigidity than hoops made with fewer larger struts. For example, a stent where the ratio of the number of struts per hoop to the strut length L (in inches) that is greater than 400 has increased rigidity.

The stent hoops can be fabricated in various different ways. In an embodiment, the Nitinol tube is loaded into a machine that cuts the predetermined pattern of the expanded hoop. Machines that can cut sheets of Nitinol are well known to those of ordinary skill in the art and are commercially available. During this machining process, the tube is typically held stationary while a cutting tool, preferably under microprocessor control, moves over the sheet and cuts the desired hoop pattern. The pattern dimensions and styles, laser positioning requirements, and other information are programmed into a microprocessor which controls all aspects of the process. The cutting tool can be a laser, laser chemical etch, water jet, electrical discharge machining, etc.

In another embodiment, a photochemical etch process may be used to cut the desired hoop pattern into the Nitinol tube. This process can include various process steps that are generally known as photolithography. A photoresist layer is deposited onto the Nitinol tube and exposing the photosensitive layer to a pattern of light that matches the desired pattern that the hoop is to be cut into. The light chemically alters the exposed areas of the photoresist layer and a chemical reaction is used to remove the portions of the photosensitive layer that were not exposed to light. An etch process then cuts through the areas of the Nitinol that are not covered by the photoresist to form the patterned medical sheet. The remaining photoresist is removed to produce the hoops.

Although the thin film tube can be used in its plane uniform thickness state, various features may also be formed in the thin film tube including slots, grooves, holes, etc. These features can cut into a solid thin film tube or formed during the thin film tube deposition process. The same machining or etching fabrication processes described above with respect to the hoops can be also be used with the thin film tube. Grooves may be formed in the thin film tube by performing a partial etch or with a mechanical tool that removes some of the thin film tube material.

The Nitinol tubes used to form the hoops and thin film tube may be formed into the desired fully expanded patterns while in the austenitic phase or in the martensitic phase. The phase of the Nitinol material is temperature dependent. In general, the austenitic transition temperature $A_f$ is between 10° C. to 50° C. about 37° C. and more preferably about 24° C. to about 37° C. At temperatures above the austenitic transition temperature, the Nitinol will be in the Austenitic phase. At lower temperatures, the Nitinol may be fully or partially in the martensitic phase. If the stent hoop pattern is cut in the martensitic phase, it can then be maintained in the expanded shape while it is heat treated to convert the Nitinol to the austenitic phase.

Figure 3:
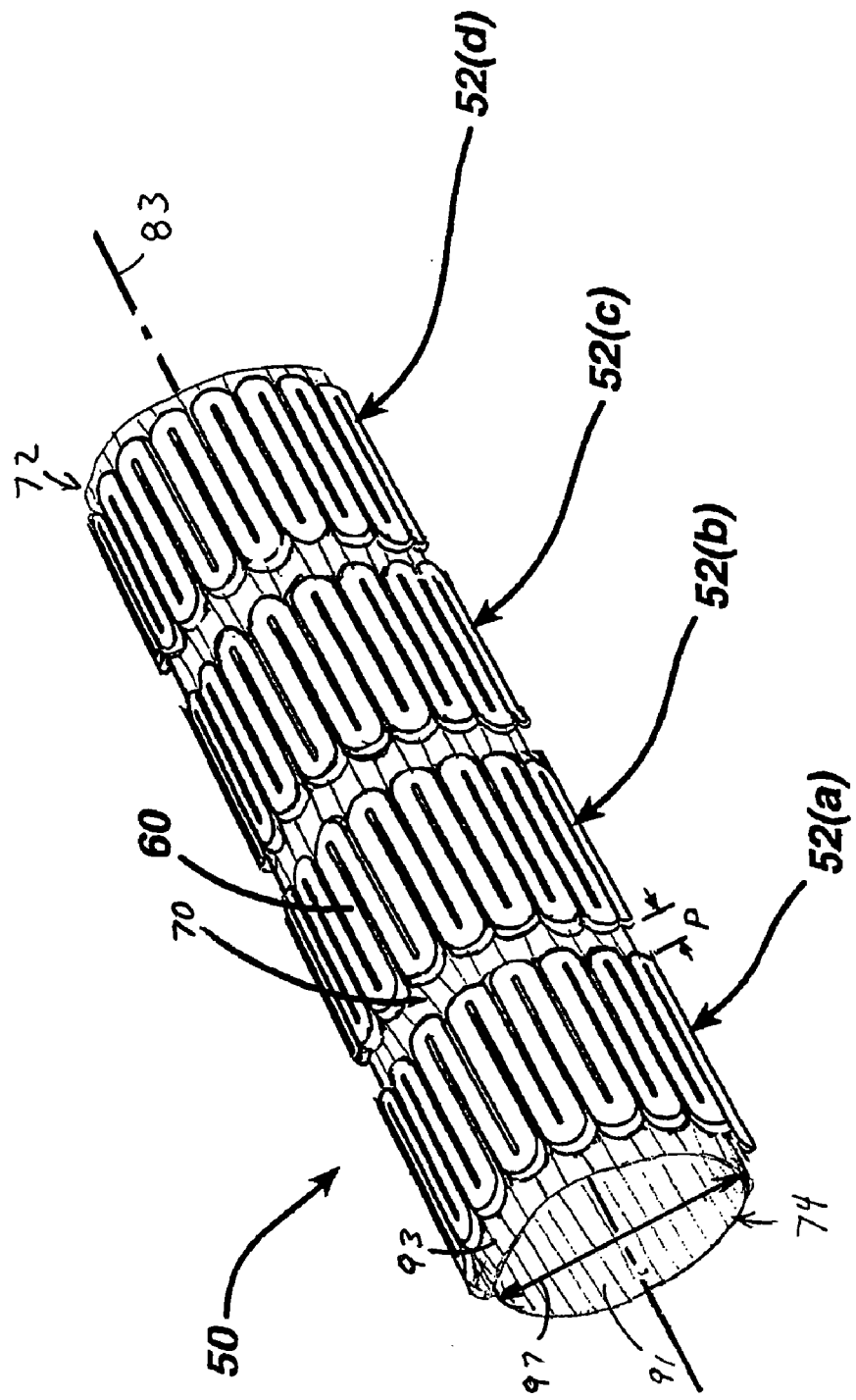
FIG. 3 is a view of an embodiment of the stent with external hoops.
Figure 4:
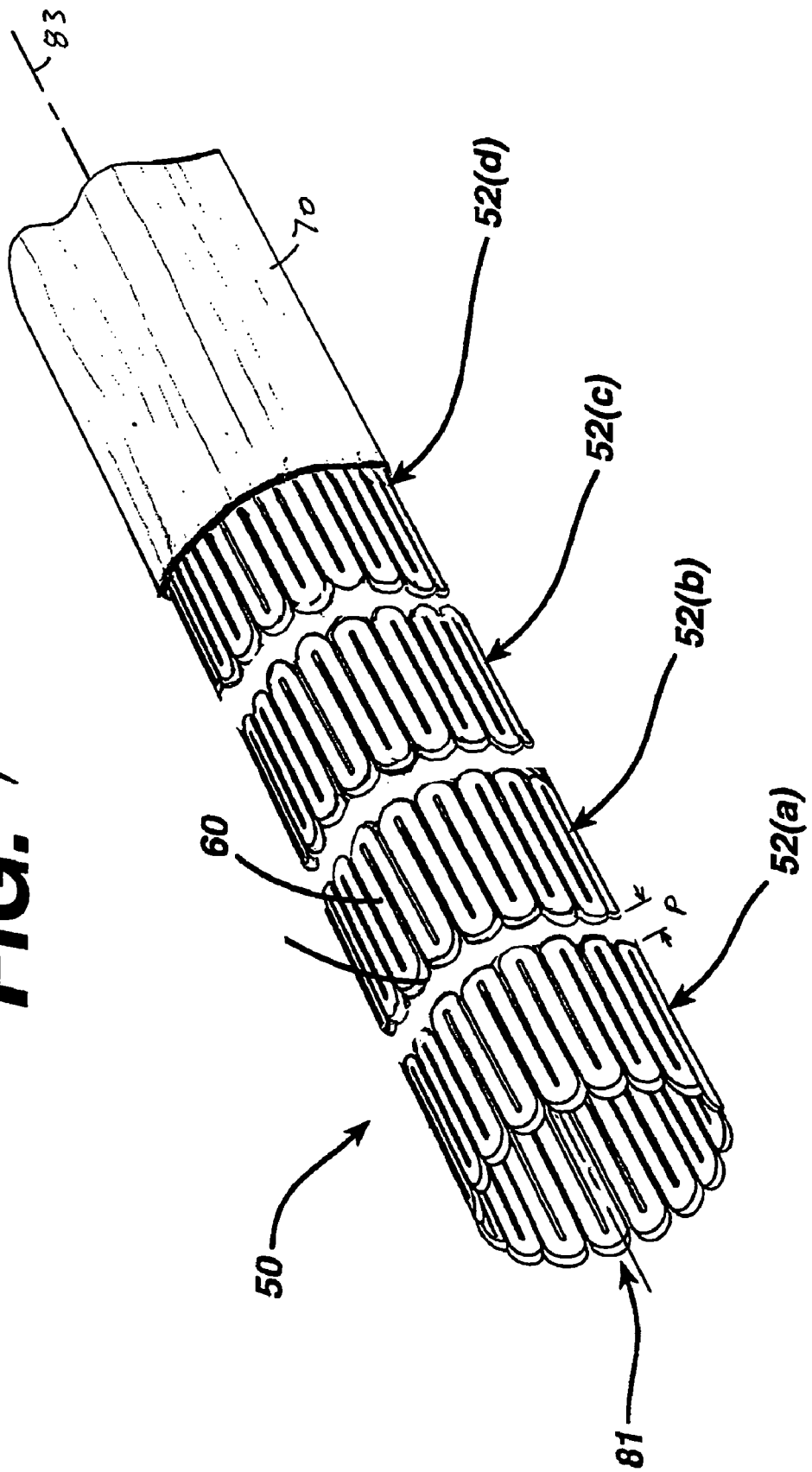
FIG. 4 is a view of an embodiment of the stent with internal hoops.
Figure 5:
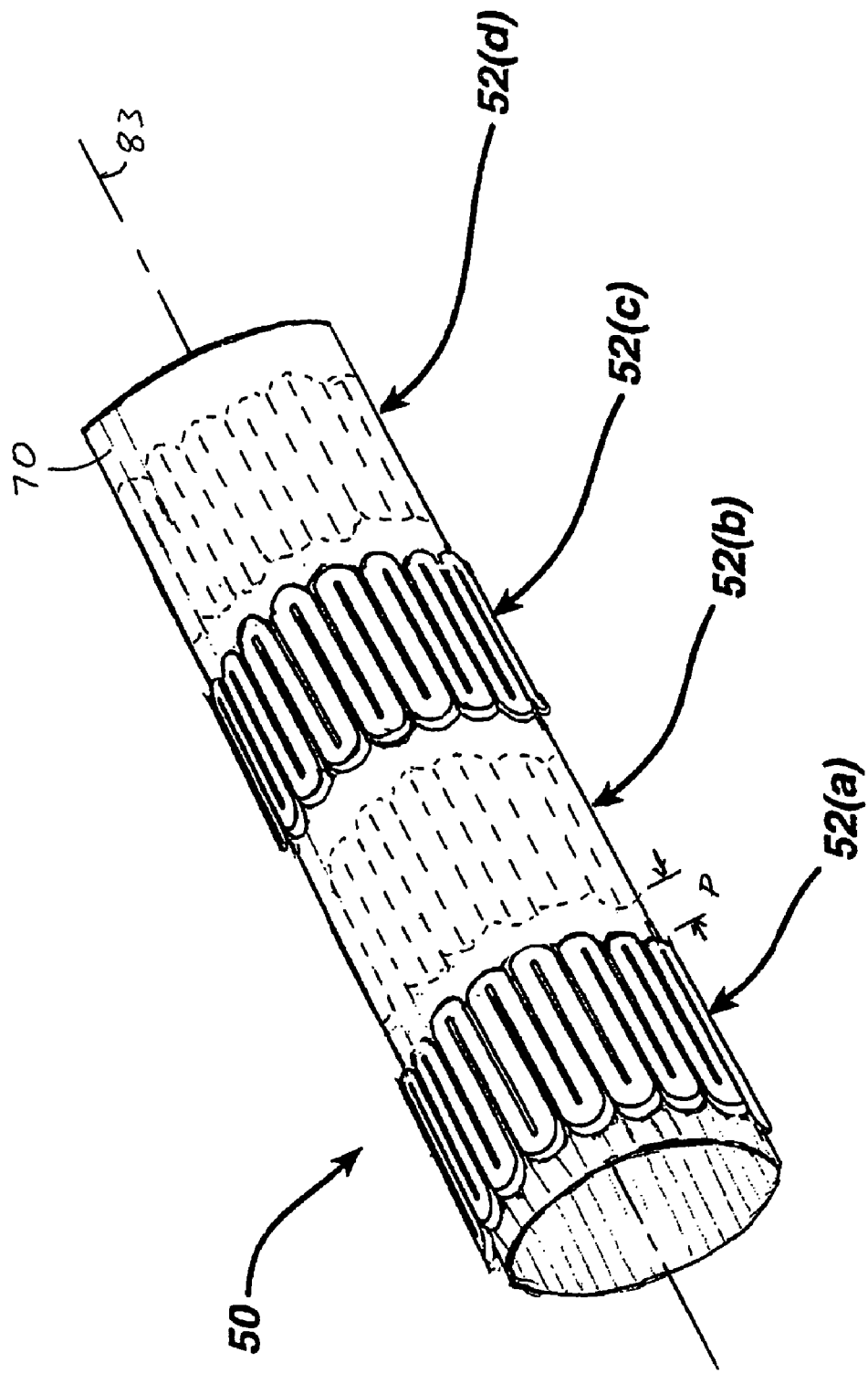
FIG. 5 is a view of an embodiment of the stent with external and internal hoops.

The inventive stent is assembled by attaching the hoops to the thin film tube. FIGS. 3-5, show three embodiments of the inventive stent 50 in its compressed state with the hoops 52(a)-52(d) attached to the thin film tube 70. The thin film tube 70 has an inner surface 91, an outer surface 93 and a longitudinal axis 83 that runs through the center of the tube between the two ends 72 and 74. The diameter 97 of the thin film tube 70 in the expanded state is similar to the diameter of the hoops 52(a)-52(d) in the expanded state.

Figure 7:
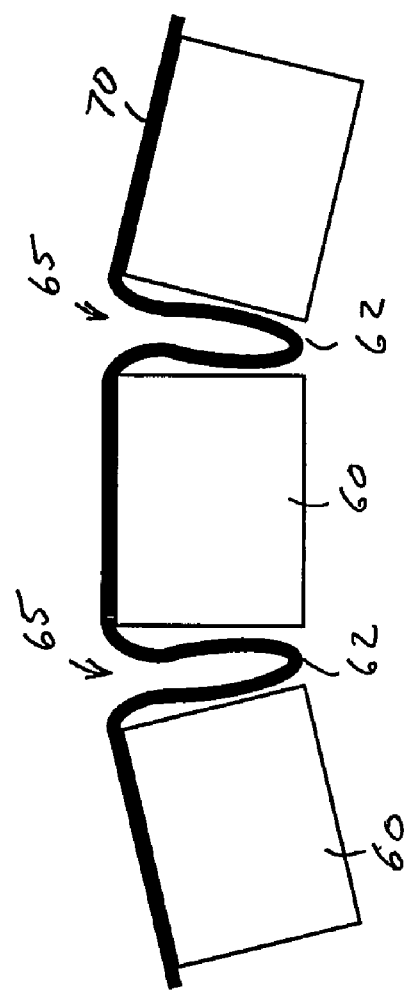
FIG. 7 is an enlarged sectional view of the stent in the expanded state.

For simplicity, FIGS. 3-5 illustrated the stents 50 as having four hoops 52(a)-52(d), however, the actual stent may have many more hoops. A longitudinal axis 83 extends through the center of the stent 50 between the ends 72 and 74. The thin film tube 70 keeps the hoops 52(a)-52(d) separated and aligned with the longitudinal axis 83. As shown in FIG. 7, when the stent 50 is compressed, small folds 62 are formed in the thin film tube 70. In the expanded state, the stent diameter expands and the thin film tube 70 is unfolded. The inventive thin film tube 70 can trap accumulate plaque and other hazardous build up between the stent and the passageway or duct.

In a first embodiment shown in FIG. 3, all of the hoops 52(a)-52(d) are attached to the outer surface 93 of thin film tube 70. The hoops 52(a)-52(d) are uniform in size and may be welded or adhesively bonded to the outer surface of the thin film tube. The hoops 52(a)-52(d) are equally spaced apart from each other along the length of the thin film tube 70. The spacing P of the hoops 52(a)-52(d) affects the stiffness of the stent 50. The stent 50 will be stiffer if the hoops 52(a)-52(d) are placed very close to each other on the thin film tube, rather than spaced farther apart.

In a second embodiment shown in FIG. 4, a stent is shown with the hoops 52(a)-52(d) attached to the inner surface 91 of the thin film tube 70. In this embodiment, the hoops 52(a)-52(d) are concealed from view by the thin film tube 70. For clarity, the thin film tube 70 is shown as partially covering hoop 52(d) and completely removed from hoops 52(a)-52(c). The thin film tube 70 provides a smooth outer surface for the stent 50 and may reduce the friction of the stent 50 as it is deployed or retracted through a tubular delivery device.

In a third embodiment shown in FIG. 5, the hoops 52(a)-52(d) are arranged in an alternating pattern along the length of the thin film tube 70. Hoops 52(a) and 52(c) are attached to the outer surface 93 while the adjacent hoops 52(b) and 52(d) are attached to the inner surface 91 of the thin film tube 70. This alternating pattern of hoops 52 coupled to the inner and outer surfaces of the thin tube 70 may continue along the length of the stent 50. In the compressed state the hoops 52(a) and 52(c) attached to the outer surface 93 of the thin film tube 70 may have a larger diameter than the hoops 52(b) and 52(d) which are attached to the inner surface 91. The thin film tube 70 may have a uniform diameter and thickness along the axial length. In other embodiments, the stent may have an arrangement of hoops that are attached to the inner and outer surfaces of the thin film tube in any pattern. For example, the stent may have pattern that includes one or more adjacent hoops mounted on the inner surface thin film tube followed by one or more adjacent hoops mounted on the outer surface.

The alternating inner and outer surface pattern of hoops may inherently prevent excessive movement of the hoops even if the hoops are not bonded to the thin film tube. The stent illustrated in FIG. 5 has a pattern of hoops mounted inside and outside the thin film tube. If the inner diameter of the outer hoops 52(a) and (c) is smaller than the outer diameter of the inner hoops 52(b) and (d), the adjacent hoops can only slide a limited distance along the thin film tube. When two adjacent hoops move close to each other, the tube is pinched between the outer diameter of one of the hoops and the inner diameter of the adjacent hoop preventing any further movement of the hoops.

The hoops are preferably attached to the thin film tube in the expanded state. As discussed, the hoops are attached to either the inner surface or the outer surface of the thin film tube. It may be easier to attach the hoops to the outer surface of the expanded thin film tube because the contact areas at the outer surface are more accessible to machinery. There are various ways in which the thin film tube can be attached to the hoops including: welding, soldering, adhesives, and mechanical coupling. In an embodiment, the hoops are welded at one or more locations at the junctions between the hoops and the thin film tube. If the hoop is welded to the thin film tube at more than one point, the weld points may be symmetrically spaced around the diameter of the hoop. For example, if two weld points are used, the welds should be on opposite sides on the hoop. If four weld points are used, the welds should be spaced at 90° intervals around the hoop. In order to avoid damage to the super elastic alloy thin film tube, special welding methods may be required. For example, laser welding is used to attach two Nitinol parts.

Contamination damage caused by environmental oxygen and nitrogen make it imperative to carry out any joining process involving melting in either a vacuum or in an inert gas atmosphere. $CO_2$ and ND:YAG laser welding can both be used to weld Nitinol. Electron beam welding can also be used to weld smaller parts together in a vacuum processing chamber. Other possible welding methods include: friction welding and fusion welding.

In an embodiment, the hoops are soldered or brazed to the thin film tube. This process requires melting a solder or brazing material which flows between the hoops and the thin film contact points and bonds the components together. In order to obtain a strong soldered or brazed bond, it may be necessary to deposit an intermediate metal layer of: nickel, copper, gold or other suitable metal surface onto the joint surfaces. This intermediate metal layer will accept the solder or brazing material with a mild flux such as a halogen based flux. Localized heat is required for soldering and brazing. In an embodiment, ultrasonic soldering with a Sn based solder may be used to bind the Nitinol parts together. Another possible method for bonding the thin film tube to the hoops is diffusion bonding.

In another embodiment, the thin film tube may be deposited directly onto the hoops so that the thin film tube is deposited and bonded to the hoops simultaneously. In this embodiment, the expanded hoops are placed on a cylindrical mandrel that holds the hoops in alignment. The thin film tube is then vapor deposited directly onto the hoops and mandrel. The deposited material is fused to the hoops during the deposition process and forms a thin film that covers the gaps between all of the struts and loops of the adjacent hoops. If the mandrel has an outer diameter that is similar to the inner diameter of the hoops, the stent will be similar to the stent illustrated in FIG. 3. In another embodiment, the outer diameter of the hoops may be held within a tube and the Nitinol thin film may be deposited on the inner surfaces of the hoops forming a film at the outer diameter of the hoops between the struts and loops. This stent is similar to the illustration in FIG. 4.

In an embodiment, adhesives are used to attach the thin film tube to the hoops. The adhesive must be biocompatible with the patient. The adhesive may be a thermal set polymer, an epoxy adhesive or any other type of biocompatible adhesive. The adhesive may be applied while the hoops and thin film tube are fully expanded to avoid applying the adhesive between adjacent struts and loops. Alternatively, the adhesive may be applied to the hoops in the compressed state to help hold the stent in the compressed state during the delivery process.

In other embodiments, mechanical connections may be used to fasten the hoops to the thin film tube. For example, the hoops and thin film tube are held together with tabs and slots. More specifically, thin tabs may be formed on the ends of the hoops on the loop sections. During the stent assembly process, the tabs are bent and placed through corresponding slots formed around the diameter of the thin film tube.

The inventive stent components are held together when the stent is compressed and during the insertion process. However, once the stent is deployed inside a passageway or duct, the connection between the hoops and thin film tube may be less critical. When the stent is deployed within the patient, the hoops expand and the bonds may be broken. As the hoop expands radially, it holds the thin film tube against the inner walls of the vessel. In the expanded state there is no need for these components to be bonded together. The stent components should not be separated if the thin film tube is mounted to the inner diameter of the hoops.

In different embodiments of the present invention, various different surface processes can be performed on the hoops and thin film tube. For example, surface processing may be performed on the stent or on the hoops and/or thin film tube individually before assembly. In one embodiment, the hoops and thin film tube may be passivated by exposing the Nitinol to oxygen to form a layer of metal oxide which helps to prevent corrosion. The hoops and thin film tube may also be polished to remove any rough surfaces through processes such as: mechanical polishing, electro polishing or chemical mechanical polishing. This polishing removes any sharp surfaces that may have been formed during the cutting processes.

Alternatively, the hoops and thin film tube may be textured to improve the adhesion of coatings applied to the stent. The texturing can be through photochemical etching, sand blasting, tumbling, etc. These textured surfaces can then be coated with different materials that will improve the stent's performance. These chemical coatings are generally intended to improve the biocompatibility of the stent within the patient's body by preventing rejection and resisting infection. These surface coatings include polymers, therapeutic agents and bioactive materials. In an embodiment, the thin film tube may be used as a drug delivery system. The thin film tube may be coated with polymers, therapeutic agents, bioactive materials which are delivered to the damaged vessel when the stent is deployed into the patient. As the stent expands, the coated thin film tube contacts the inner diameter of the vessel, delivering the coated drugs to the target area.

In an embodiment, some of the hoops and thin film tube may also be coated with a radio-opaque material that is detectable with x-rays. The radio-opaque materials may alternatively be attached to the Nitinol hoops or thin film tube by laser welding, adhesives, mechanical fasteners, etc. During or after implantation within the patient, the implant area can be x-rayed to determine the exact position of the stent. If the stent is improperly positioned, the error can be detected and corrected.

After the stent is assembled and all surface coatings are performed, the stent is ready for implantation. The stent is normally cooled below the martensitic to transform the Nitinol to the martensitic phase before the stent is compressed into a compact state for delivery into a patient. The martensitic transformation temperature $M_f$ may be between about 0° to 15° C. In the martensitic phase, the hoops and thin film tube of the stent can be compressed into a small area. As shown in FIG. 1, in the compressed shape, there may be very small gaps G between the adjacent struts and loops. The compressed Nitinol alloy will remain in the compressed shape as long as the temperature remains below the austenitic transition temperature. Because the stent must expand after deployment, the austenitic transition temperature $A_f$ is lower than the patient's body temperature.

Figure 6:
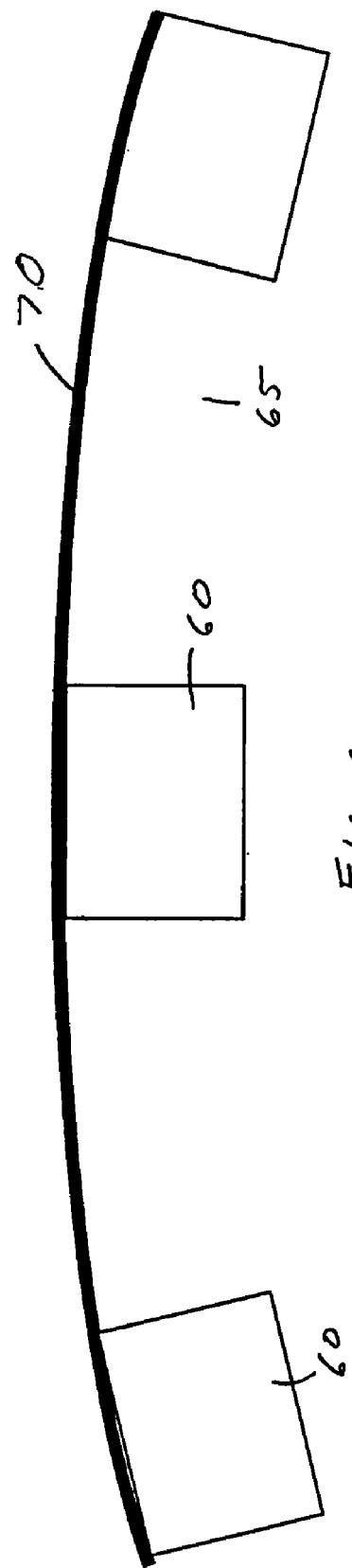
FIG. 6 is an enlarged sectional view of the stent in the expanded state.

In the compressed state, the thin film tube is preferably folded between the struts of the hoops. FIGS. 6 and 7 show a partial cross section of the stent with the thin film tube 70 attached to the outer diameter of the hoops at the struts 60 like the stent shown in FIG. 4. FIG. 6 shows the stent in the expanded state with the planar thin film tube 70 covering the gaps 65 between the adjacent struts 60 in a substantially planar manner. FIG. 7 shows the stent in the compressed state with very small gaps 65 between the adjacent struts 60. As the stent is compressed, the diameter of the thin film tube 70 must also be reduced. In the preferred embodiment, the thin film tube 70 folds axially inward between the adjacent struts 60. In this compressed configuration, the outer diameter of the compressed stent is fairly smooth because any sharp edges formed by the folded thin film 62 are bent inward. In the stent embodiment shown in FIG. 3 where the thin film tube is attached to the inner diameter of the hoops, the thin film may fold outward into the gap between the adjacent struts. Alternatively, the thin film tube may be folded away from the gaps between the struts 60 when the stent is compressed.

As discussed above, the thin film tube may have various surface features such as holes and slots. In one embodiment, the thin film tube may have grooves that help to create the inward folds between the struts. For example, grooves may be formed in the thin film tube along the inner surface close to the edges of the struts and in the outer surface in the middle of the gap between the struts. The thin film tube will tend to bend at the grooves preferably in the manner described with reference to FIG. 7.

A crimping tool is used to compress the stent onto the delivery device. In an embodiment, the crimping tool is designed to push the thin film tube between the adjacent struts as the stent is compressed. After the is compressed, the crimping tool is removed and the stent is ready for implantation with the thin film tube folded between the adjacent struts.

Figure 8:
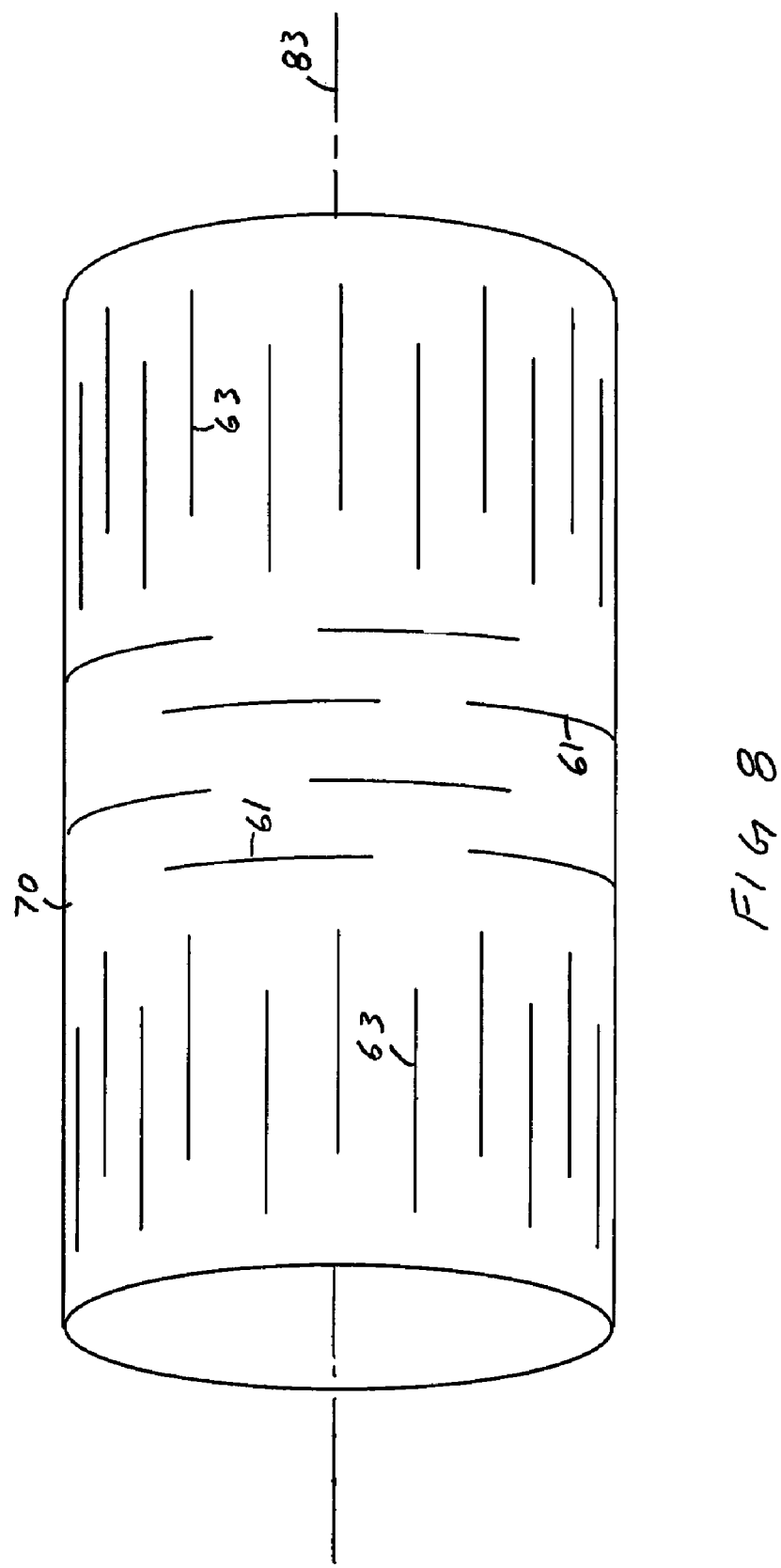
FIG. 8 is a side view of the thin film tube.

With reference to FIG. 8, the thin film tube 70 may have other features that alter the performance of the stent. For example, radial slots 61 allow the thin film tube 70 to expand and contract axially along the center axis 83 without folding or buckling. The slot separates while the thin film tube 70 is in tension and may overlap in compression. This radial slots 61 makes the stent more flexible axially so it can bend away from the central axis 83 more easily. The thin film but may also have axial slots 63 that allow the stent to be more flexible in diameter. This allows the stent to expand in diameter beyond the fully expanded outer diameter of the thin film tube 70 or contract with less folding the thin film tube 70.

The thin film tube may also have a pattern of holes that make the stent porous. This porosity is controlled by the size and concentration of holes in the thin film tube. A large concentration of large holes will be very porous while a small concentration of small holes will be much less porous. The pattern of holes may produce a stent that has variable porosity along the length. For example, the stent may be very porous at the ends which allows some blood to circulate and non-porous at the center. Alternatively, the stent may have a variable porosity around the circumference.

Figure 9:
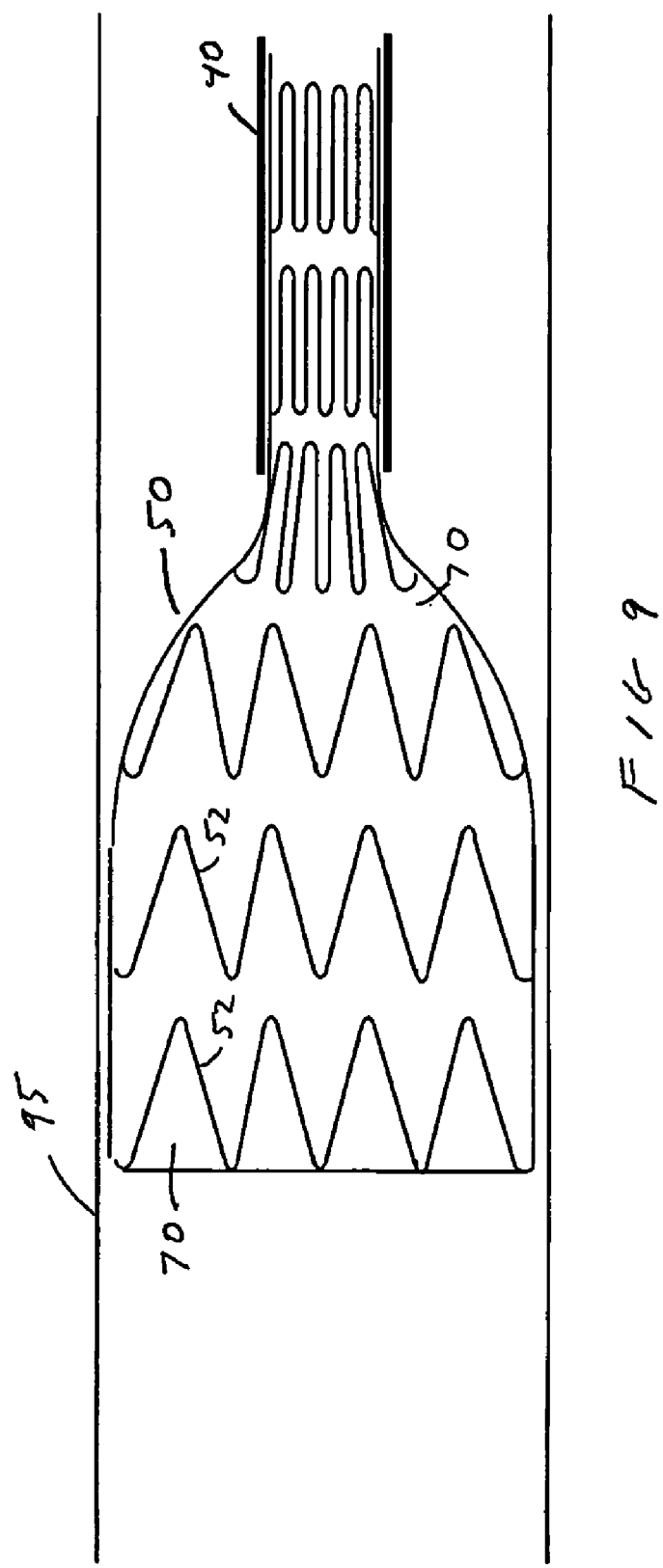
FIG. 9 is a side view of the stent partially deployed in a vessel.

The inventive stent is deployed into a vessel with a delivery apparatus. With reference to FIG. 9, the stent 50 is held in a compressed state within a sheath 40 as the delivery device moves through a patient's blood vessel to a deployment position. When the stent 50 properly positioned, the sheath 40 is retracted exposing the stent 50. With the sheath 40 removed, the hoops 52 and thin film 70 expand to the inner diameter of the vessel 95. Normally, the stent 50 is fully deployed in this manner and the delivery device is removed from the patient. However, in an embodiment, the delivery apparatus can retrieve a partially deployed stent 50 by sliding the sheath 40 back over the exposed stent 50. The sheath 40 causes stent 50 to be recompressed as it is retracted into the delivery device. When the stent is fully retracted, it can be repositioned and redeployed. This capability is useful if the stent 50 is improperly deployed within the vessel 95.

Figure 10:
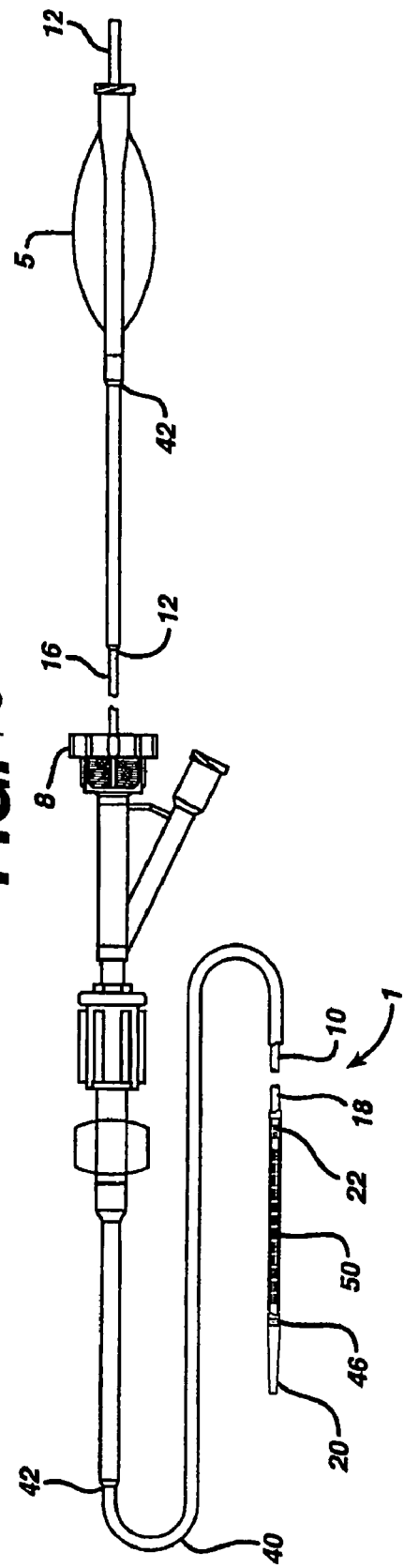
FIG. 10 is a simplified cross-sectional view of the stent delivery apparatus.
Figure 11:
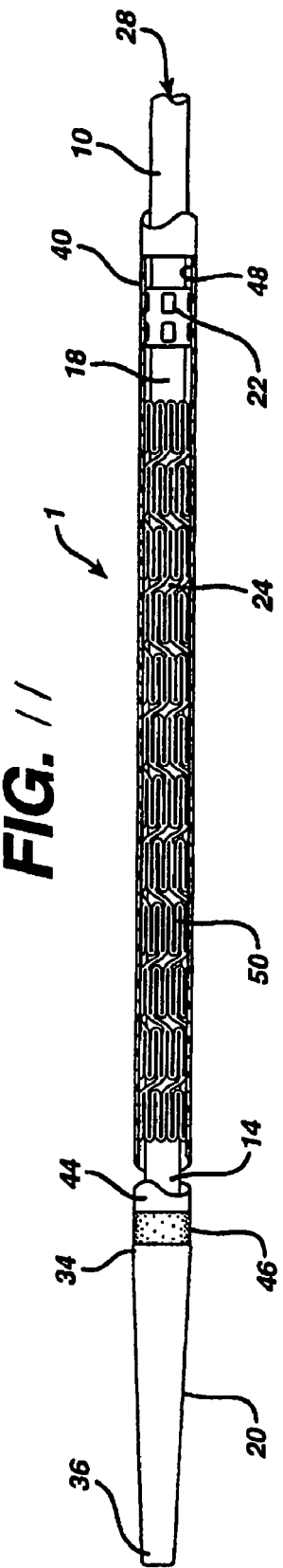
FIG. 11 is an enlarged cross-sectional view of the distal end of the delivery apparatus.

This retractable feature of the present invention can be better understood through a brief description of a delivery apparatus, as shown in FIGS. 10 and 11. The delivery apparatus 1 comprises inner and outer coaxial tubes. The inner tube is called the shaft 10 and the outer tube is called the sheath 40. Shaft 10 has proximal and distal ends 12 and 14 respectively. The distal end 14 of the shaft terminates at a luer lock hub 5. Preferably, shaft 10 has a proximal portion 16 which is made from a relatively stiff material such as stainless steel, Nitinol, or any other suitable material, and an distal portion 18 which is made from a polyethylene, polyimide, pellethane, Pebax, Vestamid, Cristamid, Grillamid or any other suitable material known to those of ordinary skill in the art. The two portions are joined together by any number of means known to those of ordinary skill in the art. The stainless steel proximal end gives the shaft the necessary rigidity or stiffness it needs to effectively push out the stent, while the polymeric distal portion provides the necessary flexibility to navigate tortuous vessels.

The distal portion 18 of the shaft has a distal tip 20 attached thereto. The distal tip 20 has a proximal end 34 whose diameter is substantially the same as the outer diameter of the sheath 40. The distal tip tapers to a smaller diameter from its proximal end to its distal end, wherein the distal end 36 of the distal tip has a diameter smaller than the inner diameter of the sheath. Also attached to distal portion 18 of shaft 10 is a stop 22 which is proximal to the distal tip 20. Stop 22 can be made from any number of materials known in the art, including stainless steel, and is even more preferably made from a highly radiopaque material such as platinum, gold tantalum. The diameter of stop 22 is substantially the same as the inner diameter of sheath 40, and would actually make frictional contact with the inner surface of the sheath. Stop 22 is releasably coupled to the end of the stent 50 and helps to push the stent 50 out of the sheath during deployment, and helps the stent from migrating proximally into the sheath 40.

A stent bed 24 is defined as being that portion of the shaft between the distal tip 20 and the stop 22. The stent bed 24 and the stent 50 are coaxial so that the portion of shaft 18 comprising the stent bed 24 is located within the lumen of the stent 50. However, the stent bed 24 does not make any contact with stent 50 itself Lastly, shaft 10 has a guidewire lumen 28 extending along its length from its proximal end 12 and exiting through its distal tip 20. This allows the shaft 10 to receive a guidewire much in the same way that an ordinary balloon angioplasty catheter receives a guidewire. Such guidewires are well known in art and help guide catheters and other medical devices through the vasculature of the body.

Sheath 40 is preferably a polymeric catheter and has a proximal end 42 terminating at a hub 52. Sheath 40 also has a distal end 44 which terminates at the proximal end 34 of distal tip 20 of the shaft 18, when the stent is in its fully un-deployed position. The distal end 44 of sheath 40 includes a radiopaque marker band 46 disposed along its outer surface. As will be explained below, the stent is fully deployed when the marker band 46 is lined up with radiopaque stop 22, thus indicating to the physician that it is now safe to remove the apparatus 1 from the body. Sheath 40 preferably comprises an outer polymeric layer and an inner polymeric layer. Positioned between outer and inner layers a braided reinforcing layer. Braided reinforcing layer is preferably made from stainless steel. The use of braided reinforcing layers in other types of medical devices can be found in U.S. Pat. Nos. 3,585,707 issued to Stevens on Jun. 22, 1971, 5,045,072 issued to Castillo et al. on Sep. 3, 1991, and U.S. Pat. No. 5,254,107 issued to Soltesz on Oct. 19, 1993, all of which are hereby incorporated herein by reference.

FIGS. 10 and 11 show the stent 50 as being in its fully un-deployed position. This is the position the stent is in when the apparatus 1 is inserted into the vasculature and its distal end is navigated to a target site. Stent 50 is disposed around stent bed 24 and at the distal end 44 of sheath 40. The distal tip 20 of the shaft 10 is distal to the distal end 44 of the sheath 40, and the proximal end 12 of the shaft 10 is proximal to the proximal end 42 of the sheath 40. The stent 50 is in a compressed state and makes frictional contact with the inner surface 48 of the sheath 40.

When being inserted into a patient, sheath 40 and shaft 10 are locked together at their proximal ends by a Touhy Borst valve 8. This prevents any sliding movement between the shaft and sheath which could result in a premature deployment or partial deployment of the stent. When the stent 50 reaches its target site and is ready for deployment, the Touhy Borst valve 8 is opened so that that the sheath 40 and shaft 10 are no longer locked together.

The method under which apparatus 1 deploys stent 50 should be readily apparent. The apparatus 1 is first inserted into a vessel so that the stent bed 24 is at a target diseased site. Once this has occurred the physician would open the Touhy Borst valve 8. The physician would then grasp the proximal end 12 of shaft 10 so as to hold it in place. Thereafter, the physician would grasp the proximal end 42 of sheath 40 and slide it proximal, relative to the shaft 40. Stop 22 prevents the stent 50 from sliding back with the sheath 40, so that as the sheath 40 is moved back, the stent 50 is pushed out of the distal end 44 of the sheath 40. Stent deployment is complete when the radiopaque band 46 on the sheath 40 is proximal to radiopaque stop 22. The apparatus 1 can now be withdrawn through stent 50 and removed from the patient.

In the retractable embodiment, the stop 22 is releasably coupled to the stent 50. If the stent 50 is properly positioned, the physician actuates a release mechanism and the stop 22 releases the stent 50 into the patient before removing the delivery apparatus 1. If a partially deployed stent 50 needs to be recovered, the physician would hold the proximal end 12 of shaft 10 in place and slide the proximal end 42 of the sheath 40 to retract the stent 50 back within the sheath 40. After the stent 50 is fully retracted, the delivery device 1 can be repositioned and the stent 50 can be redeployed as described above.

In an alternative embodiment, delivery device can cut the stent to a desired length when a cutting mechanism is actuated by the physician. As discussed above, the hoops of the inventive stent are held together by a thin film tube. In this embodiment, the delivery device only deploys a portion of the stent. After the desired length of the stent has been deployed into the patient, it can shorten the stent at one of the thin film sections between the adjacent hoops still in the delivery device. The delivery device may include one or more small blades that cuts through of the thin film around the diameter between two adjacent hoops. The blades may extend radially and may also rotate within the delivery device to cut the thin film portion of the stent. The blades are located within the sheath and do not come in contact with the patient. After the stent is cut and fully deployed in the patient, the delivery device and the unused portion of the stent are removed from the patient.

In other embodiments, the stent may be broken by pulling two adjacent hoops apart until the thin film tube tears. In this embodiment, the delivery device has a mechanical device is used to separate the hoops that are adjacent to the section of thin film that is to be torn. The thin film material will tear if an applied stress exceeds the ultimate tensile strength of the thin film tube. The thin film may be perforated or have a groove that reduces the forces needed to break the thin film of the stent 50. After the stent 50 is cut or broken, it is fully deployed in the vessel of the patient before the delivery device is removed.

For indications such as threatened vessel closure, suboptimal PTCA results, etc., that require a drug-eluting platform with minimal radial strength, the balloon expansion stent delivery method may be used for improved placement accuracy. In this embodiment, the thin film tube is attached to the outer diameter of a series of hoops. The tube and hoops are then crimped onto the balloon expansion delivery device. In the crimped state, the smaller diameter, the thin film tube would have a sufficient radial force to constrain the super elastic hoops in the compressed diameter for delivery. Thus, the crimped stent on the balloon delivery device can be positioned within the patient in-vivo. When the stent is properly positioned, the balloon is inflated to expand the hoops and thin film tube. In its expanded geometry, the thin film tube would not interfere with the superelastic behavior of the stent hoops allowing the stent to perform as intended.

The described balloon expansion delivery method can be achieved by plastically deforming the thin film tube when fully expanded to the final diameter or by any other means of geometric design. In the expanded state, the thin film tube may have thinner and smaller features. The thin film tube may be martensitic or austenitic to optimize the strength balance between the stents and the thin film tube.

Figure 12:
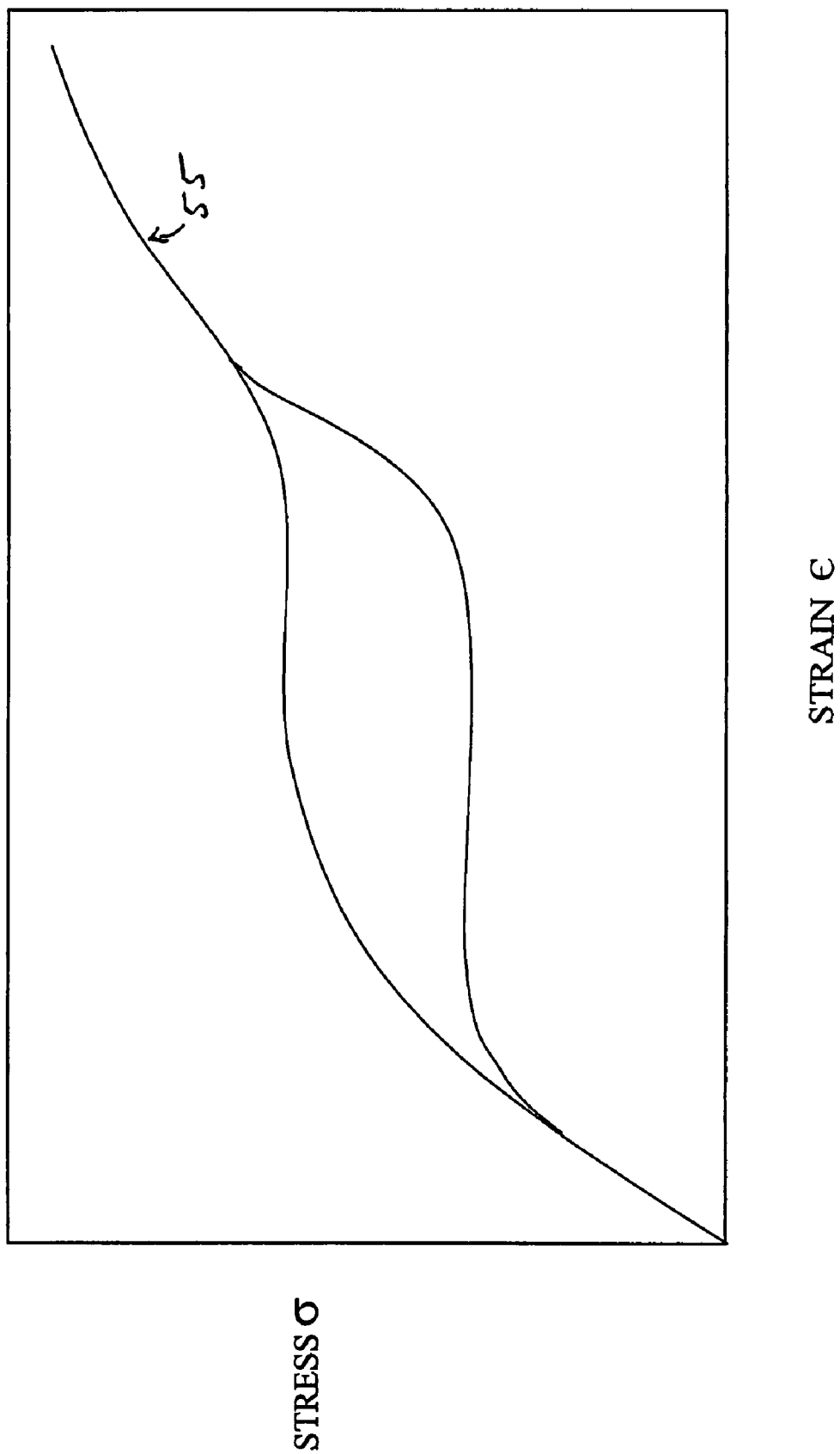
FIG. 12 is a stress strain curve for super elastic alloys such as Nitinol.

For indications that do not require the stent to be crush resistant and require only a minimal amount of recoverable strain, the thin film tube in the martensitic phase or possibly the austenitic phase. With reference to FIG. 12, the thin film tube could then be strained during the expansion of the stent to reach the second elastic portion 55 of the Nitinol stress-strain curve. The thin film tube material would be deformed to maintain its expanded diameter, yet provide elastic recovery and possibly fatigue resistance for small amounts of alternating strain.

As shown in the figures, the geometry of the inventive stent changes significantly from the compressed state to its fully expanded state. Referring to FIG. 2, as the stent expands, the strut angle α and strain levels in the struts and loops are affected. Preferably, all of the struts and loops will strain in a predictable manor so that the stent is structurally reliable and uniform in strength. In addition, it is preferable to minimize the maximum strain experienced by struts and loops, since Nitinol's mechanical strength properties are generally limited by strain rather than by stress like most metal materials. Most metals have a linear relationship between stress and strain in an elastic region and break after the stress exceeds the maximum tensile strength of the metal.

In contrast, when stress is applied to a specimen of a metal such as Nitinol exhibiting super elastic characteristics at a temperature above which the austenite is stable (i.e. the temperature at which the transformation of martensite phase to the austenite phase is complete), the specimen deforms elastically until it reaches a particular stress level where the alloy then undergoes a stress-induced phase transformation from the austenite phase to the martensite phase. As the phase transformation proceeds, the alloy undergoes significant increases in strain but with little or no corresponding increases in stress. The strain increases while the stress remains essentially constant until the transformation of the austenite phase to the martensite phase is complete. Thereafter, further increases in stress are necessary to cause further deformation. The martensitic metal first deforms elastically upon the application of additional stress and then plastically with permanent residual deformation.

If the load on the specimen is removed before any permanent deformation has occurred, the martensitic phase specimen will elastically recover and transform back to the austenite phase. The reduction in stress first causes a decrease in strain. As stress reduction reaches the level at which the martensite phase transforms back into the austenite phase, the stress level in the specimen will remain essentially constant (but substantially less than the constant stress level at which the austenite transforms to the martensite) until the transformation back to the austenite phase is complete, i.e. there is significant recovery in strain with only negligible corresponding stress reduction. The alloys are structurally stronger and more rigid in the austenitic phase than the martensitic phase.

After the transformation back to austenite is complete, further stress reduction results in elastic strain reduction. This ability to incur significant strain at relatively constant stress upon the application of a load and to recover from the deformation upon the removal of the load is commonly referred to as super elasticity or "shape memory." See for example, U.S. Pat. No. 4,665,906 (Jervis) and U.S. Pat. No. 4,925,445 (Sakamoto et al.).

The transition between martensite and austenite phases can be controlled by the material temperature. The shape material is fully martensitic when it is colder than the final martensitic transition temperature $M_f$ and fully austenitic when the material is heated above the final austenitic transition temperature $A_f$. The alloy may be partially martensitic and partially austenitic at temperatures between the final martensitic transition temperature $M_f$ and the final austenitic transition temperature $A_f$. These shape memory alloys are stronger in the full austenitic phase than in the martensitic state, but no longer have the super elastic property. When a shape memory alloy structure is heated, it reverts, or attempts to revert, to its original heat-stable shape.

The super elastic metal alloys may comprise nickel, titanium and additional elements such as: niobium, hafnium, tantalum, tungsten and gold. The ratio of the nickel and titanium in the super elastic alloy will alter the martensite/austenite transition temperatures. An alloy having more than 50.5 atomic % nickel has a complete transition temperature from the martensite phase to the austenite phase ($A_f$) below human body temperature, so that austenite is the only stable phase at body temperature. The alloy preferably has an $A_f$ in the range from about 24° C. to about 37° C. The $M_f$ is about 25° to 50° C. lower than the $A_f$.

Because these super elastic alloys are capable of extreme deformation, it is desirable to design products that will not exceed the maximum allowable strain during use. In trying to minimize the maximum strain experienced by the struts and loops, the present invention utilizes a structural geometry that distributes strain to areas of the stent which are less susceptible to failure. For example with reference to FIGS. 1 and 2, one of the most vulnerable areas of the stent 50 is the inside surface S of the connecting loops 62 defined by the inner radius which undergoes the most deformation and therefore has the highest level of strain of all the stent features. This area is also critical in that it is usually compressed into the smallest radius on the tissue repair matrix. Stress concentrations are minimized by designing the loops 62 with the largest radii possible and/or have a smaller change in angle α between the compressed and fully expanded states shown in FIG. 2.

Nitinol can withstand extremely large amounts of elastic strain deformation, so the above features are well suited to a stent made from this alloy. This feature allows for maximum utilization of Nitinol or other material capabilities to enhance radial strength, improve stent strength uniformity, improves fatigue life by minimizing local strain levels and improves stent apposition in irregular organ wall shapes and curves.

Although particular embodiments of the present invention have been shown and described, modification may be made to the device and/or method without departing from the spirit and scope of the present invention. The terms used in describing the invention are used in their descriptive sense and not as terms of limitations.

What is claimed is:

1. A stent for insertion into a vessel of a patient, the stent comprising: a) a tubular member having front and back open ends and a longitudinal axis extending therebetween, the tubular member having a first smaller diameter for percutaneous insertion into the vessel and a second larger diameter for deployment in the vessel; b) the tubular member comprising a structural frame having a plurality of only discrete, independent, and unconnected adjacent hoops having inner and outer diameters and extending between the front and back ends of the tubular member, the hoops comprise a plurality of longitudinal struts and a plurality of loops connecting adjacent struts each of the plurality of longitudinal struts having a luminal surface, an abluminal surface, and side walls extending between the luminal and abluminal surfaces; and c) a metallic thin film tube having inner and outer diameters, the thin film tube being affixed to at least a portion of the hoops and holding the plurality of hoops apart from each other and in alignment with the longitudinal axis, wherein when the tubular member is in the first smaller diameter, the thin film tube is folded axially inward between at least some circumferentially adjacent longitudinal struts, so as to extend past the abluminal surface and in between the side walls of the circumferentially adjacent longitudinal struts, the portions of the folded thin film tube containing bends defining a bending line, and the bending line being parallel to the longitudinal axis.

2. The stent according to claim 1 wherein the inner diameter of the thin film tube is attached to the outer diameters of at least some of the plurality of adjacent hoops.

3. The stent according to claim 1 wherein the outer diameter of the thin film tube is attached to the inner diameter of at least some of the plurality of adjacent hoops.

4. The stent according to claim 1 wherein the thin film tube is attached to some of the hoops with a welded connection.

5. The stent according to claim 1 wherein the thin film tube is attached to some of the hoops with an adhesive bond.

6. The stent according to claim 5 wherein the thin film tube has a larger pore size at an end of the thin film tube than in the center of the thin film tube.

7. The stent according to claim 1 wherein the thin film tube is attached to some of the hoops with a mechanical connection.

8. The stent according to claim 1 wherein a portion of the thin film tube is porous.

9. The stent according to claim 1 wherein the thin film tube is cut in a pattern to improve radial and longitudinal flexibility of the stent.

10. The stent according to claim 9 wherein the thin film tube is cut in a pattern to improve the flexibility of the stent.

11. A stent for insertion into a vessel of a patient, the stent comprising: a) a tubular member having front and back open ends and a longitudinal axis extending therebetween, the tubular member having a first smaller diameter for percutaneous insertion into the vessel and a second larger diameter for deployment in the vessel; b) the tubular member comprising a structural frame having a plurality of only discrete, independent and unconnected adjacent hoops made from a superelastic nickel titanium alloy, the hoops having an inner and outer surface defining a thickness there between, and extending between the front and back ends of the tubular member, the hoops comprise a plurality of longitudinal struts and a plurality of loops connecting adjacent struts; and c) a metallic thin film tube made from a superelastic nickel titanium alloy affixed to at least a portion of the hoops, the thin film tube having inner and outer diameters and holding the plurality of hoops apart from each other and in alignment with the longitudinal axis, wherein when the tubular member is in the first smaller diameter, the thin film tube is folded between at least some circumferentially adjacent longitudinal struts so as to extend into an area circumferentially adjacent the hoop thickness, the portions of folded thin film tube containing bends defining a bending line, and the bending line being parallel to the longitudinal axis.

12. The stent according to claim 11 wherein the inner diameter of the thin film tube is attached to the outer diameters of at least some of the plurality of adjacent hoops.

13. The stent according to claim 11 wherein the outer diameter of the thin film tube is attached to the inner diameter of at least some of the plurality of adjacent hoops.

14. The stent according to claim 11 wherein the thin film tube is attached to some of the tubular member with a welded connection.

15. The stent according to claim 11 wherein the loops and struts have widths which are less than the thickness of the hoops.

16. The stent according to claim 1 or 11 wherein the thin film tube is vapor deposited onto and bonded to at least some of the tubular members.

* * * * *